United States Patent
Zhang et al.

(10) Patent No.: US 8,604,065 B2
(45) Date of Patent: Dec. 10, 2013

(54) PYRIDYL CYANOGUANIDINE DERIVATIVES

(75) Inventors: Hesheng Zhang, Tianjin (CN); Xin Chen, Tianjin (CN); Yingwei Chen, Tianjin (CN); Junjie Cong, Tianjin (CN); Xingwen Li, Tianjin (CN)

(73) Assignee: Hesheng Zhang, Tianjian (CN)

( * ) Notice: Subject to any disclaimer, the term of this patent is extended or adjusted under 35 U.S.C. 154(b) by 0 days.

(21) Appl. No.: 13/577,218

(22) PCT Filed: Nov. 18, 2010

(86) PCT No.: PCT/CN2010/078868
§ 371 (c)(1),
(2), (4) Date: Aug. 3, 2012

(87) PCT Pub. No.: WO2011/095027
PCT Pub. Date: Aug. 11, 2011

(65) Prior Publication Data
US 2012/0309797 A1    Dec. 6, 2012

(30) Foreign Application Priority Data

Feb. 4, 2010   (WO) ................ PCT/CN2010/000156

(51) Int. Cl.
*C07D 213/75* (2006.01)
*C07C 277/08* (2006.01)
*A61K 31/44* (2006.01)
*A61K 31/155* (2006.01)

(52) U.S. Cl.
USPC ............ 514/353; 514/634; 546/306; 564/104

(58) Field of Classification Search
None
See application file for complete search history.

(56) References Cited

U.S. PATENT DOCUMENTS

2012/0029036 A1    2/2012   Zhang et al.

FOREIGN PATENT DOCUMENTS

| CN | 1258278 A | 6/2000 |
|---|---|---|
| CN | 1509283 A | 6/2004 |
| WO | 98/54146 A1 | 12/1998 |
| WO | 02/094813 A1 | 11/2002 |
| WO | 2010/088842 A2 | 8/2010 |

OTHER PUBLICATIONS

Beauparlant, et al., "Preclinical Development of the Nicotinamide Phosphoribosyl Transferase Inhibitor Prodrug GMX1777," *Anti-Cancer Drugs*, 2009, 20:346-354.
Johanson et al., "Antitumoural Effects of the Pyridyl Cyanoguanidine CHS 828 on Three Different Types of Neuroendocrine Tumours Xenografted to Nude Mice," *Neuroendocrinology*, 2005; 82:171-176.
Vig Hjarnaa, et al., "CHS 828 a Novel Pyridyl Cyanguanidine with Potent Antitumour Activity in Vitro and in Vivo," *Cancer Research*, 59, 5751-5757, Nov. 15, 1999.
Phatak et al., "Antimetabolites," Poster Session Oct. 24, 2008, 150.
The International Search Report from PCT/CN2010/078868, dated Mar. 30, 2011 and English Translation copy.

*Primary Examiner* — Zinna Northington Davis
(74) *Attorney, Agent, or Firm* — Kilpatrick Townsend & Stockton LLP

(57) ABSTRACT

Compounds of formula (I) or pharmaceutically acceptable salts thereof, and use for treating cancer thereof are disclosed, wherein, the definitions of X, Y, $R_1$, $R_2$ and n are described in description.

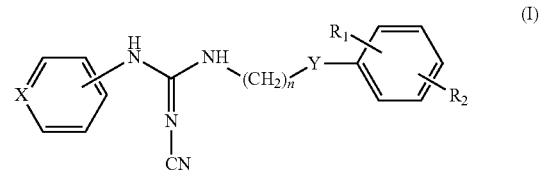

16 Claims, No Drawings

PYRIDYL CYANOGUANIDINE DERIVATIVES

CROSS-REFERENCE TO RELATED APPLICATIONS

This application is the U.S. National Stage entry of PCT/CN2010/078868, filed Nov. 18, 2010, which claims priority to International Application No. PCT/CN2010/000156, filed Feb. 4, 2010, the disclosures of each are herein incorporated by reference.

TECHNICAL FIELD

The invention relates to guanidines and use thereof, and particularly to pyridyl cyanoguanidine derivatives and use thereof.

TECHNICAL BACKGROUND

It has been reported by the prior art that the pyridyl cyanoguanidines have anti-tumour activities. For example, U.S. Pat. No. 5,563,160 discloses a series of pyridyl cyanoguanidines which inhibit cancer cells. However, only experimental data of several compounds in the general formula were provided in the patent.

The inventors of the present application conducted a research on pyridyl cyanoguanidines, and found that some pyridyl cyanoguanidines with particular structures had unexpected biological activities. The present application is thereby provided.

SUMMARY OF THE INVENTION

In one aspect, the present application relates to a compound of formula (I) or a pharmaceutically acceptable salt thereof,

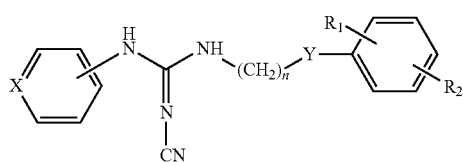

wherein: X is N or CH;
n is an integer from 3 to 10;
Y is —O—, —S—, —NR$_3$—, —OC(O)— or —NR$_3$C(O)—, wherein R$_3$ is H or C$_{1-6}$ alkyl;
R$_1$ is methoxy substituted with one or more F or Cl, preferably methoxy substituted with at least two F or Cl at 2- or 3-position of the benzene ring;
R$_2$ is H, C$_{1-6}$ alkyl, C$_{1-6}$ alkoxy, hydroxy, cyano, nitro, formamido, aminosulfonyl, halogen, C$_{1-6}$ alkyl optionally substituted with halogen, or C$_{1-6}$ alkoxy optionally substituted with halogen.

In another aspect, the present application relates to a pharmaceutical composition, comprising a therapeutically effective amount of a compound of formula (I) or a pharmaceutically acceptable salt thereof as defined above and a pharmaceutically acceptable carrier.

In another aspect, the present application relates to use of a compound of formula (I) or a pharmaceutically acceptable salt thereof in the preparation of a medicament for the treatment of cancer.

In another aspect, the present application relates to a method for preparing a compound of formula (I) or a pharmaceutically acceptable salt thereof, comprising reacting a compound of formula (II)

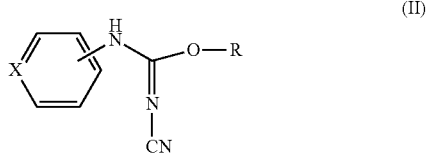

with a compound of formula (III)

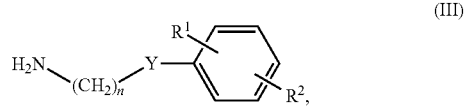

preferably in the presence of a base,
wherein, R is C$_{1-6}$ alkyl, aryl, or aryl substituted with halogen or C$_{1-6}$ alkyl, X, Y, n, R$_1$ and R$_2$ have the same meanings as defined above, and optionally, converting the resulting compound of formula (I) into a pharmaceutically acceptable salt thereof.

In another aspect, the present application also relates to a method for inhibiting growth of tumour cells, comprising administering to the tumour cells an inhibitory effective amount of a compound of formula (I) or a pharmaceutically acceptable salt thereof or a pharmaceutical composition as defined above.

In another aspect, the present application further relates to a method for treating tumour in a subject, comprising administering to the subject a therapeutically effective amount of a compound of formula (I) or a pharmaceutically acceptable salt thereof or a pharmaceutical composition as defined above.

Upon research, the inventors have found that if the end benzene ring in the compound as shown in formula (I) is substituted with at least one methoxy substituted with at least one F or Cl, preferably at 2- or 3-position, particularly at 2-position, the resulting compounds have surprisingly high cell avtivites compared to compounds with other substituents. In addition, the compounds of formula (I) in the present application have improved hydrophilia, and therefore have an advantage in forming corresponding formulations.

DESCRIPTION OF THE INVENTION

In the above definitions and the following embodiments of compounds of formula (I), the terms used herein have the following meanings:

The term "C$_{1-6}$ alkyl" refers to a straight or branched saturated hydrocarbon radical having 1-6 carbon atoms, and is preferably C$_{1-4}$ alkyl having 1-4 carbon atoms. Examples of C$_{1-6}$ alkyl include, but are not limited to, methyl, ethyl, propyl, isopropyl, butyl, isobutyl, 1-methylpropyl, t-butyl, pentyl, isopentyl, 1,2-dimethylpropyl, 2,2-dimethylpropyl, hexyl, isohexyl, etc.

The term "C$_{1-6}$ alkoxy" refers to a straight or branched saturated alkoxy group having 1-6 carbon atoms, and is preferably C$_{1-4}$ alkoxy having 1-4 carbon atoms. Examples of C$_{1-6}$ alkoxy include, but are not limited to, methoxy, ethoxy, propoxy, isopropoxy, butoxy, isobutoxy, 1-methylpropoxy, t-butoxy, pentoxy, isopentoxy, 1,2-dimethylpropoxy, 2,2-dimethylpropoxy, hexoxy, isohexoxy, etc.

The term "aryl" refers to a monocyclic or condensed aromatic cyclic group containing 6-20 carbon atoms. Non-limiting examples of aryl include phenyl and naphthyl.

The term "halogen" refers to fluorine, chlorine, bromine or iodine.

The term "pharmaceutical composition" as used in the present application refers to a formulation formed by a compound of the present application and a medium generally accepted in the art for the delivery of the biologically active compound to mammals, such as humans. Such a medium includes all pharmaceutically acceptable carriers.

The term "pharmaceutically acceptable carrier" as used in the present application refers to various carriers which have no adverse effect on forming a pharmaceutical composition, which include, but are not limited to, any adjuvant, excipient, glidant, sweetening agent, diluent, preservative, dye/colorant, flavor enhancer, surfactant, wetting agent, dispersant, suspending agent, stabilizer, isotonic agent, disintegrating agent, solvent or emulsifier, which are approved by the United States Food and Drug Administration (FDA) as being acceptable for use in humans or animals.

The terms "inhibitory effective amount" and "therapeutically effective amount" are interchangeably used in the present application, and refer to the amount of a compound of the present application which, when administered to a subject, preferably a mammal, more preferably a human, is sufficient to effectively inhibit tumour cells or treat tumour. The amount of a compound of the present application constituting a "inhibitory effective amount" or "therapeutically effective amount" will vary depending on the selected compound, condition of the subject to be administered to, but can be determined routinely by those skilled in the art on the basis of their own knowledge and this disclosure in view of common knowledge in the art.

The term "treating" or "treatment" refers to the administration of the compound or formulation of the invention for preventing, ameliorating or eliminating diseases or one or more symptoms associated therewith, and includes:

(i) preventing the disease or condition from occurring in a mammal, particularly when such mammal is predisposed to the condition but has not yet been diagnosed as having it;

(ii) inhibiting the disease or condition, i.e., arresting its development;

(iii) relieving the disease or condition, i.e., causing regression of the disease or condition.

"Pharmaceutically acceptable salt" includes "pharmaceutically acceptable acid addition salt" and "pharmaceutically acceptable base addition salt".

The term "pharmaceutically acceptable acid addition salt" refers to those salts which retain the biological effectiveness and properties of the free bases, which are biologically or otherwise desirable, and which are formed with inorganic acids such as, but are not limited to, hydrochloric acid, hydrobromic acid, sulfuric acid, nitric acid, phosphoric acid and the like, and organic acids such as, but are not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, naphthalene-1,5-disulfonic acid, naphthalene-2-sulfonic acid, 1-hydroxy-2-naphthoic acid, nicotinic acid, oleic acid, orotic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

The term "pharmaceutically acceptable base addition salt" refers to those salts which retain the biological effectiveness and properties of the free acids, which are biologically or otherwise desirable. These salts are prepared from addition of an inorganic base or an organic base to the free acid. In the present application, salts derived from inorganic bases are preferred and include, but are not limited to, sodium, potassium, lithium salts, etc.

One aspect of the present application provides a compound of formula (I) or a pharmaceutically acceptable salt thereof,

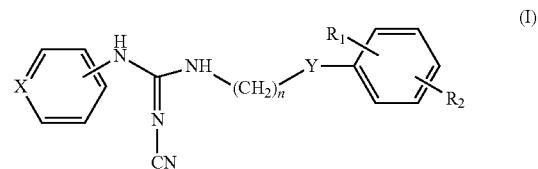

wherein: X is N or CH;

n is an integer from 3 to 10;

Y is —O—, —S—, —NR$_3$—, —OC(O)— or —NR$_3$C(O)—, wherein R$_3$ is H or C$_{1-6}$ alkyl;

R$_1$ is methoxy substituted with one or more F or Cl, preferably methoxy substituted with at least two F or Cl at 2- or 3-position of the benzene ring;

R$_2$ is H, C$_{1-6}$ alkyl, C$_{1-6}$ alkoxy, hydroxy, cyano, nitro, formamido, aminosulfonyl, halogen, C$_{1-6}$ alkyl optionally substituted with halogen or C$_{1-6}$ alkoxy optionally substituted with halogen.

In some preferred embodiments of the compound of formula (I) in each aspect of the present application, R$_1$ is methoxy substituted with at least two F or Cl, preferably methoxy substituted with two F, most preferably trifluoromethoxy.

In some preferred embodiments, R$_1$ is at 2-position of the benzene ring.

In other preferred embodiments, X is N. More preferably, N is at para-position of the guanidino.

In some other embodiments, Y is —O—, —S—, —NR$_3$—, —OC(O)— or —NR$_3$C(O)—, wherein R$_3$ is H or methyl; preferably, Y is —O—, —NR$_3$—, —OC(O)— or —NR$_3$C(O)—, wherein R$_3$ is H or methyl; more preferably, Y is —O—, —NH— or —OC(O)—; most preferably, Y is —O—.

In some other embodiments, n is an integer from 4 to 8.

In some further embodiments, R$_2$ is H, C$_{1-6}$ alkyl, C$_{1-6}$ alkoxy, hydroxy, nitro, formamido, halogen, C$_{1-6}$ alkyl optionally substituted with halogen or C$_{1-6}$ alkoxy optionally substituted with halogen; preferably, R$_2$ is H, C$_{1-6}$ alkyl, nitro, halogen, or C$_{1-6}$ alkyl optionally substituted with halogen; more preferably, R$_2$ is H, C$_{1-4}$ alkyl, nitro, halogen; most preferably, R$_2$ is H, C$_{1-4}$ alkyl, F, Cl, or Br.

In some embodiments of the compound of formula (I) in each of the above aspects of the present application, X is N;

n is an integer from 4 to 8;

Y is —O—, —S—, —NR$_3$—, —OC(O)— or —NR$_3$C(O)—, wherein R$_3$ is H or C$_{1-6}$ alkyl;

R$_1$ is methoxy substituted with at least two F, preferably methoxy substituted with at least two F at 2-position of the benzene ring;

R$_2$ is H, C$_{1-6}$ alkyl, nitro, halogen, or C$_{1-6}$ alkyl optionally substituted with halogen.

In some other embodiments of the compound of formula (I) in each of the above aspects of the present application, X is N;

n is an integer from 4 to 8;

Y is —O—, —NH— or —OC(O)—;

R$_1$ is methoxy substituted with at least two F, preferably methoxy substituted with at least two F at 2-position of the benzene ring;

R$_2$ is H, C$_{1-4}$ alkyl, nitro, or halogen.

In some other embodiments of the compound of formula (I) in each of the above aspects of the present application, X is N;

n is an integer from 4 to 8;

Y is —O—, —NH— or —OC(O)—;

R$_1$ is OCF$_3$ or OCHF$_2$, preferably OCF$_3$ or OCHF$_2$ at 2-position of the benzene ring;

R$_2$ is H, C$_{1-4}$ alkyl, F, Cl or Br.

In some other embodiments of the compound of formula (I) in each of the above aspects of the present application, X is N;

n is an integer from 4 to 8;

Y is —O—;

R$_1$ is OCF$_3$ or OCHF$_2$, preferably OCF$_3$ or OCHF$_2$ at 2-position of the benzene ring;

R$_2$ is H, C$_{1-4}$ alkyl, F, Cl or Br.

In another embodiment, the present application provides the following compounds of formula (I) or pharmaceutically acceptable salts thereof:

N-cyano-N'-(6-(2-difluoromethoxy-5-chlorophenoxy)hexyl)-N''-(4-pyridyl)guanidine;

N-cyano-N'-(6-(o-trifluoromethoxyphenoxy)hexyl)-N''-(3-pyridyl)guanidine;

N-cyano-N'-(6-(m-trifluoromethoxyphenoxy)hexyl)-N''-(4-pyridyl)guanidine;

N-cyano-N'-(6-(p-trifluoromethoxyphenoxy)hexyl)-N''-(4-pyridyl)guanidine;

N-cyano-N'-(5-(o-trifluoromethoxyphenoxy)pentyl)-N''-(4-pyridyl)guanidine;

N-cyano-N'-(8-(o-trifluoromethoxyphenoxy)octyl)-N''-(4-pyridyl)guanidine;

N-cyano-N'-(6-(2-trifluoromethoxy-4-bromophenoxy)hexyl)-N''-(4-pyridyl)guanidine;

N-cyano-N'-(6-(o-trifluoromethoxyanilino)hexyl)-N''-(4-pyridyl)guanidine;

N-cyano-N'-(6-(o-trifluoromethoxybenzoyloxy)hexyl)-N''-(4-pyridyl)guanidine;

N-cyano-N'-(6-(2-difluoromethoxy-5-tertbutylphenoxy)hexyl)-N''-(4-pyridyl)guanidine;

N-cyano-N'-(6-(o-trifluoromethoxyphenoxy)hexyl)-N''-(4-pyridyl)guanidine;

N-cyano-N'-(6-(2-difluoromethoxy-4-chlorophenoxy)hexyl)-N''-(4-pyridyl)guanidine;

N-cyano-N'-(6-(2-trifluoromethoxy-4-chlorophenoxy)hexyl)-N''-(4-pyridyl)guanidine;

N-cyano-N'-(6-(2-trifluoromethoxy-4-nitrophenoxy)hexyl)-N''-(4-pyridyl)guanidine;

N-cyano-N'-(6-(2-trifluoromethoxy-4-fluorophenoxy)hexyl)-N''-(4-pyridyl)guanidine;

N-cyano-N'-(6-(5-methyl-2-difluoromethoxyphenoxy)hexyl)-N''-(4-pyridyl)guanidine;

N-cyano-N'-(6-(2-difluoromethoxyphenoxy)hexyl)-N''-(4-pyridyl)guanidine;

N-cyano-N'-(6-(2-difluoromethoxy-5-fluorophenoxy)hexyl)-N''-(4-pyridyl)guanidine.

The present application also provides a pharmaceutical composition, comprising a therapeutically effective amount of a compound of formula (I) or a pharmaceutically acceptable salt thereof in the present application and a pharmaceutically acceptable carrier. In some embodiments, the pharmaceutical composition is used for treating cancer.

The compound of formula (I) or a pharmaceutically acceptable salt thereof and the pharmaceutical composition in the present application can inhibit tumour cells in mammals, preferably humans. The tumour includes, but is not limited to, pancreatic cancer, acute lymphoblastic leukemia, lung cancer, such as adenocarcinoma of lung, pharyngeal squamous cell carcinoma, lymphoma, stomach cancer, breast cancer, melanoma, neuroendocrine tumour, intestinal cancer, multiple myeloma, fibrosarcoma, prostate cancer or liver cancer. Accordingly, the compound of formula (I) or a pharmaceutically acceptable salt thereof in the present application can be promisingly used as a medicament for treating the above tumours (cancers).

The pharmaceutical composition comprises a therapeutically effective amount of a compound of formula (I) or a pharmaceutically acceptable salt thereof and a pharmaceutically acceptable carrier. The therapeutically effective amount in the composition can be determined by a person skilled in the art based on the selected compound and the condition of the subject to be administered to. In some embodiments, the effective amount can be 0.01-99.99% by weight of the composition, preferably 0.1-75%, more preferably 0.5-50%.

The pharmaceutical composition of the present application can be formulated into various formulations for therapeutical administration via various routes of administration. For example, the pharmaceutical composition can be formulated into a formulation suitable for topical, oral, intravenous, or intramuscular administration. The formulation can be administered to a subject or patient in need thereof via various routes of administration including oral, buccal, rectal, parenteral, intraperitoneal, subcutaneous, transdermal, and endotracheal administration.

The formulation for topical administration can be in the form of a transdermal patch, suppository, paste, lotion, ointment, gel, etc. The topical formulation can comprise one or more penetrants, thickeners, diluents, emulsifiers, dispersants, or binders. When the composition is formulated for transdermal delivery, the composition can be formulated with a penetration enhancer in a composition or used together with it. The penetration enhancers include chemical and physical penetration enhancers which can promote the dermatic delivery of the composition.

When the composition is formulated with a chemical penetration enhancer, the penetration enhancer is selected from those matched with the compound and is present in an amount sufficient to promote the dermatic delivery of the compound in a subject, for example in an amount sufficient to promote the delivery of the compound in the systemic circulation of the subject.

For oral formulation, the compound can work alone or be combined with suitable additives for preparing tablets, powders, granules and capsules. For example, the compound can be combined with a conventional additive, such as lactose, mannitol, corn starch, or potato starch; a blending agent, such as crystalline cellulose, cellulose derivatives, gum arabic, corn starch, or gelatin; a disintegrating agent, such as corn starch, potato starch or sodium carboxymethylcellulose; a lubricant, such as talc or magnesium stearate; if necessary, a diluent, a buffer, a wetting agent, a preservative, and a flavoring agent. Especially advantageously, combination of the compound with a buffer can provide a protection of the compound against the gastric acid environment at low pH. Also preferably provided is an intestinal coating to avoid the sediment of the compound in stomach.

The compound of the invention can be formulated into an injection formulation by dissolving, suspending, or emulsifying in a water soluble or insoluble solution (such as plant oil or other similar oils, synthetic fatty acid glyceride, higher aliphatic acid ester or propylene glycol). If necessary, the compound of the invention can be combined with conventional additives (such as solubilizer, isotonic agent, suspending agent, emulsifier, stabilizer and preservative). Particularly beneficial solubilizers include vitamine E TPGS (d-a-tocopherol polyethylene glycol 1000 succinate), cyclodextrin, etc.

In another aspect, the present application relates to a method for preparing a compound of formula (I) or a pharmaceutically acceptable salt thereof, comprising reacting a compound of formula (II)

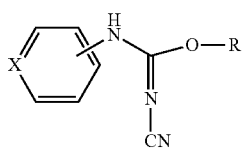

with a compound of formula (III)

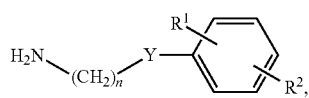

wherein, R is $C_{1-6}$ alkyl or aryl or aryl substituted with halogen or $C_{1-6}$ alkyl, X, Y, n, $R_1$ and $R_2$ have the same meanings as defined above, and optionally, converting the resulting compound of formula (I) into a pharmaceutically acceptable salt thereof.

The molar ratio of the compound of formula (II) to the compound of formula (III) can be 1:1. However, it is understood that an excess of one over the other will be advantageous to the yield of the final product. Generally, the molar ratio of the compound of formula (II) to the compound of formula (III) can be in the range of from 1.2 to 1.5:1.

In some preferred embodiments of the preparation method in the present application, the reaction is performed in the presence of a base. The base can be an organic base, preferably tertiary amine, such as triethylamine, pyridine. The molar ratio of the base to the reference reactant can be 1.5-2.5:1.

The reaction can be performed in a polar organic solvent that is inert to the reaction, preferably a solvent with higher polarity. As non-limited examples, preferred solvents are as follows: lower alkyl alcohols such as methanol, ethanol, propanol; amides such as dimethylformamide, dimethyl acetamide; sulphones such as dimethyl sulfoxide, sulfolane; ethers such as tetrahydrofuran; and acetonitrile, etc.

The temperature of the above reaction is not limited, and is generally room temperature. Preferably, the reaction system is under the protection of inert gas.

In another aspect, the present application further relates to a method for inhibiting the growth of tumour cells, comprising administering to the tumour cells an inhibitory effective amount of a compound of formula (I), a pharmaceutically acceptable salt thereof, or a pharmaceutical composition as defined above.

In another aspect, the present application further relates to a method for treating tumour in a subject, comprising administering to the subject a therapeutically effective amount of a compound of formula (I), a pharmaceutically acceptable salt thereof, or a pharmaceutical composition as defined above.

EXAMPLES

The following non-limited examples aim to enable those skilled in the art to more clearly understand and carry out the invention. They should not be construed as limiting the scope of the invention.

Preparation of Intermediates 1a. 5-chloro-2-difluoromethoxyphenol 723 mg (5.0 mmol) of sodium chlorodifluoroacetate, 220 mg (5.5 mmol) of sodium hydroxide and 838 mg (5.5 mmol) of 4-chlorocatechol were successively added to a mixture of 7.0 mL of N,N-dimethylformamide and 0.1 mL of water under argon atmosphere with stirring. The mixture was slowly heated to 125° C. and allowed to react at this temperature for 1.0 h. The reaction was stopped and cooled to room temperature. To the reaction solution was added 10 mL of 1.0 mol/L hydrochloric acid until the solution turned acid, and then 50 mL of water and 20 mL of ethyl acetate were added. The organic layer was isolated, and the water layer was extracted with 20 mL×2 of ethyl acetate. The organic layers were combined, successively washed with 50 mL of water and 50 mL of saturated saline, dried over anh. $MgSO_4$, filtered and concentrated. The residue was purified by preparative silica gel thin layer chromatography (mobile phase: petroleum ether: ethyl acetate=4:1) to obtain 189 mg of a light yellow oil. Yield 19.4%. MS([M-H]$^-$): 193.

Compounds 1b (5-t-butyl-2-difluoromethoxyphenol) and 1c (5-methyl-2-difluoromethoxyphenol) were prepared with processes similar to that for preparing compound 1a.

1d. 4-nitro-2-trifluoromethoxyphenol 3.0 g (7.5 mmol) of anh. bismuth nitrate was added to a solution of 891 mg (5.0 mmol) of 2-trifluoromethoxyphenol in 20 mL of tetrahydrofuran (redistilled) under argon atmosphere with stirring. The mixture was slowly heated to 50° C. and allowed to react at this temperature for 10 min. The reaction was stopped, cooled, filtered under reduced pressure and the filter cake was washed with 20 mL of tetrahydrofuran. The filtrate was concentrated, and 40 mL of water and 45 mL of ethyl acetate were added. The organic layer was isolated, and the water layer was extracted with 40 mL×2 of ethyl acetate. The organic layers were combined, successively washed with 110 mL of water and 110 mL of saturated saline, dried over anh. $MgSO_4$, filtered and concentrated. The residue was purified by silica column chromatography (mobile phase: petroleum ether: ethyl acetate=15:1) to obtain 346 mg of a yellow oil. Yield 31.4%.

1e. 4-amino-2-trifluoromethoxyphenol 223 mg (1.0 mmol) of 4-nitro-2-trifluoromethoxyphenol, 224 mg (4.0 mmol) of reduced iron powder, and 321 mg (6.0 mmol) of ammonia chloride were successively added to a mixture of 20 mL of ethanol and 6.0 mL of water under argon atmosphere with mechanical stirring. The mixture was slowly heated to 50° C. and allowed to react at this temperature for 1.5 h until the solution turned brown. The reaction was stopped, naturally cooled, filtered under reduced pressure, and the filter cake was washed with 10 mL of ethyl acetate. 20 mL of water and 20 mL of ethyl acetate were added to the filtrate. The organic layer was isolated, and the water layer was extracted with 20 mL×2 of ethyl acetate. The organic layers were combined, successively washed with 50 mL of water and 50 mL of saturated saline, dried over anh. MgSO$_4$, filtered and concentrated to obtain 144 mg of a dark red solid. Yield 74.4%.

1f. 4-fluoro-2-trifluoromethoxyphenol 33 mg (0.48 mmol) of sodium nitrite was added to a solution of 77 mg (0.4 mmol) of 4-amino-2-trifluoromethoxyphenol in 0.8 mL of 65% (w/w) hydrofluoric acid/pyridine under argon atmosphere with stirring at an outer bath temperature of 0~5° C. The outer bath was heated to 5~10° C. and the mixture was stirred for 30 min until the solution turned brownish red. To the above solution were successively added 90 mg (0.4 mmol) of stannous chloride dihydrate and 105 mg (0.4 mmol) of tetrabutylammonium fluoride trihydrate. The solution was slowly heated to_100° C., allowed to react at this temperature for 3.0 h until it was dark brown. The reaction was stopped, naturally cooled, poured into ice water, and 15 mL of ethyl acetate was added. The organic layer was isolated, and the water layer was extracted with 15 mL×2 of ethyl acetate. The organic layers were combined, successively washed with 30 mL of water and 30 mL of saturated saline, dried over anh. MgSO$_4$, filtered and concentrated. The residue was purified by preparative silica gel thin layer chromatography (mobile phase: petroleum ether: ethyl acetate=2:1) to obtain 14 mg of a pale yellow oil. Yield 17.9%.

1g. p-chloro-o-trifluoromethoxyphenol 1.78 g of o-trifluoromethoxyphenol was dissolved in 5 mL of toluene, and the mixture was stirred in an ice water bath for 20 min. 1.485 g of sulfonyl chloride was added dropwise to the reaction system within 10 min, which was then stirred for 20 min. The solution was moved to a water bath maintained at 30° C., and allowed to stir at this temperature for 1 h. 200 mL of 5% sodium carbonate aqueous solution and 50 mL of toluene were added to the system, which was then violently vibrated and isolated (pH of water layer was 10 upon determination). The pH of water layer was adjusted to 2 with 2 N of hydrochloric acid aqueous solution. The solution was extracted with 50 mL of toluene once again. The toluene layers were combined, successively washed with 100 mL of water and 100 mL of saturated sodium chloride aqueous solution, dried over 5 g of anh. MgSO$_4$ for 30 min, and concentrated via a rotary evaporator to obtain a white granular solid. MS anion peak (M-H: 213).

2a. 6-amino tert-butyl formate-hexyl p-toluenesulfonate 5.85 g (0.05 mol) of 6-aminohexanol was added to 30 mL of dichloromethane (treated with molecular sieve) in an ice bath with stirring, and the solid was not dissolved completely. A solution of 12.0 g (0.055 mol) of di-tert-butyl dicarbonate in 20 mL of dichloromethane (treated with molecular sieve) was added dropwise to the above solution to obtain a white turbid mixture, which was allowed to react at room temperature for 2.5 h. The reaction was stopped, and 50 mL of water was added. The organic layer was isolated, and the water layer was extracted with 50 mL×2 of dichloromethane. The organic layers were combined, successively washed with 125 mL of 5.0% citric acid aqueous solution, 125 mL of saturated sodium bicarbonate aqueous solution and 125 mL of saturated saline, dried over anh. MgSO$_4$, filtered and concentrated to obtain a pale yellow oil 10.9 mg which was directly used in the next step.

The product as obtained above (0.05 mol) and 11.4 g (0.06 mol) of p-toluenesulfonyl chloride were added to 50 mL of dichloromethane (treated with molecular sieve) in an ice bath with stirring, and the solid was dissolved completely. 12.1 mL (0.15 mol) of pyridine was added dropwise to the above solution, which was then allowed to stir at room temperature overnight. The reaction was stopped, and 50 mL of water was added. The organic layer was isolated, and the water layer was extracted with 50 mL×2 of dichloromethane. The organic layers were combined, successively washed with 125 mL of 5.0% citric acid aqueous solution, 125 mL of water and 125 mL of saturated saline, dried over anh. MgSO$_4$, filtered, concentrated and dried under vacuum to obtain 13.9 mg of a white solid. Yield 74.7%.

Compound 2b (6-(t-butoxycarbonylamino)hexyl 2-(trifluoromethoxy)benzoate) was prepared with a process similar to that for preparing compound 2a.

3a. tert-butyl 6-(5-chloro-2-difluoromethoxy-phenoxy) hexyl carbamate 189 mg (0.97 mmol) of 5-chloro-2-difluoromethoxyphenol and 47 mg (1.94 mmol) of sodium hydride were added to 3.0 mL of N,N-dimethylformamide in an ice bath under argon atmosphere with stirring, and the solution was further stirred for 1.0 h. A solution of 721 mg (1.94 mmol) of 6-amino tert-butyl formate-hexyl p-toluenesulfonate in 3.0 mL of N,N-dimethylformamide was added dropwise to the above solution, which was then allowed to stir at room temperature overnight. The reaction was stopped, and 40 mL of ethyl acetate and 100 mL of water was added. The organic layer was isolated, and the water layer was extracted with 40 mL×2 of ethyl acetate. The organic layers were combined, successively washed with 120 mL of saturated sodium bicarbonate aqueous solution, 120 mL of water and 120 mL of saturated saline, dried over anh. MgSO$_4$, filtered and concentrated. The residue was purified by silica column chromatography (mobile phase: petroleum ether: ethyl acetate=15:1) to obtain 198 mg of a pale yellow oil. Yield 51.8%. MS([M+Na]$^+$): 416.

Compound 3b (t-butyl 6-(2-(trifluoromethoxy)phenylamino)hexyl carbamate) was prepared with a process similar to that for preparing compound 3a.

4a. 6-(5-chloro-2-difluoromethoxy-phenoxy)hexyl-1-amine 0.6 mL (8.0 mmol) of trifluoroacetic acid was added to a solution of 198 mg (0.5 mmol) of tert-butyl 6-(5-chloro-2-difluoromethoxy-phenoxy) hexyl carbamate in 5.0 mL of dichloromethane (treated with molecular sieve) in an ice bath under argon atmosphere with stirring. Bubbles were produced and the mixture was stirred for 3.0 h. The reaction was stopped, and the solvent was distilled off via a rotary evaporator. 10 mL of 5.0 mol/L sodium hydroxide was added to the residue until the solution turned basic. 15 mL of ethyl acetate was added. The organic layer was isolated, and the water layer was extracted with 15 mL×2 of ethyl acetate. The organic layers were combined, successively washed with 40 mL of water and 40 mL of saturated saline, dried over anh. MgSO$_4$, filtered and concentrated to obtain 144 mg of a pale yellow oil. Yield 98.0%.

Compounds 4b-4t were synthesized with similar methods:

4b. 6-(2-(trifluoromethoxy)phenoxy)hexyl-1-amine 4c. 6-(3-(trifluoromethoxy)phenoxy)hexyl-1-amine 4d. 6-(4-(trifluoromethoxy)phenoxy)hexyl-1-amine 4e. 5-(2-(trifluoromethoxy)phenoxy)pentyl-1-amine 4f. 6-(4-bromo-2-(trifluoromethoxy)phenoxy)hexyl-1-amine 4g. N-(6-aminohexyl)-2-(trifluoromethoxy)aniline 4h. 6-aminohexyl 2-(trifluoromethoxy)benzoate 4i. 6-(3-t-butyl-2-(difluoromethoxy)phenoxy)hexyl-1-amine 4j. 6-(4-chloro-2-(difluoromethoxy)phenoxy)hexyl-1-amine 4k. 6-(4-chloro-2-(trifluoromethoxy)phenoxy)hexyl-1-amine 4l. 6-(4-nitro-2-(trifluoromethoxy)phenoxy)hexyl-1-amine 4m. 6-(4-fluoro-2-(trifluoromethoxy)phenoxy)hexyl-1-amine 4n. 6-(3-methyl-2-(difluoromethoxy)phenoxy)hexyl-1-amine 4o. 6-(2-(difluoromethoxy)phenoxy)hexyl-1-amine 4p. 6-(3-fluoro-2-(difluoromethoxy)phenoxy)hexyl-1-amine 4q. 5-(2-(methoxy)phenoxy)pentyl-1-amine 4r. 6-(4-chlorophenoxy)hexyl-1-amine 4s. 6-(2-chlorophenoxy)hexyl-1-amine 4t. 6-(2-(methoxy)phenoxy)hexyl-1-amine 5a. 1-cyano-2-phenyl-3-(pyrid-4-yl)-isourea 10.0 g (0.042 mol) of diphenyl-N-cyanocarbonate and 2.44 g (0.026 mol) of 4-aminopyridine were successively added to 10 mL of tetrahydrofuran (redistilled) under argon atmosphere with stirring, and the mixture was slowly heated to 50° C. and allowed to react at this temperature for 2.5 h. The solid was dissolved completely. The reaction was cooled to room temperature and stirred overnight. The reaction was stopped, placed in a refrigeratory for 20 min, filtered under reduced pressure to obtain 4.7 g of a solid. Yield 75.9%.

Compound 5b (1-cyano-2-phenyl-3-(pyrid-3-yl)-isourea) was synthesized by the method for preparing compound 5a.

6. 2-(7-hydroxyheptyl)isoindol-1,3-dione 585 mg of 7-bromoheptanol was dissolved in 5 mL of DMF. 833 mg of potassium phthalimidate was added, and the mixture was stirred for 4 h. 50 mL of water and 50 mL of DCM were added to the reaction system, which was violently vibrated and then isolated. The water layer was once again extracted with 50 mL of DCM. The two organic layers were combined, successively washed with 100 mL of water and 100 mL of saturated sodium chloride aqueous solution, dried over 5 g of anh. MgSO$_4$ for 30 min, and concentrated via a rotary evaporator to obtain a pale yellow transparent oily liquid.

7. 7-(1,3-dioxoisoindol-2-yl)heptyl-4-methylbenzenesulfonate 783 mg of 2-(7-hydroxyheptyl)isoindol-1,3-dione was added to 40 mL of DCM, and 800 mg of p-toluenesulfonyl chloride was added. Pyridine was then added dropwise with stirring, and the mixture was stirred overnight. After 24 h, 100 mL of water was added to the reaction system, which was then violently vibrated and isolated. The water layer was extracted with 50 mL of DCM. The organic layers were combined, successively washed with 100 mL of 5% citric acid aqueous solution, 100 mL of saturated sodium carbonate aqueous solution, and 100 mL of saturated sodium chloride aqueous solution, dried over 5 g of MgSO$_4$ for 30 min, and concentrated via a rotary evaporator to obtain an oily liquid.

8. 2-(7-(2-methoxyphenoxy)heptypisoindol-1,3-dione 745 mg of o-methoxyphenol was dissolved in 10 mL of DMF. 144 mg of sodium hydride was added, and the mixture was stirred for 20 min. 1.25 g of 7-(1,3-dioxoisoindol-2-yl)heptyl-4-methylbenzenesulfonate was added to the reaction system, which was then stirred overnight. After 16 h, 50 mL of water and 50 mL of ethyl acetate were added to the reaction system, which was then violently vibrated and isolated. The water layer was extracted with 50 mL of ethyl acetate. The organic layers were combined, successively washed with 100 mL of saturated sodium carbonate aqueous solution and 100 mL of saturated sodium chloride aqueous solution, dried over 5 g of MgSO$_4$ for 30 min, and concentrated via a rotary evaporator to obtain a yellowish-brown oil. The oil was purified by flash column chromatograph eluted with ethyl acetate: n-hexane 1:2 to obtain 500 mg of a yellow transparent oil.

9a. 7-(2-methoxyphenoxy)heptyl-1-amine 500 mg of 2-(7-(2-methoxyphenoxy)heptyl)isoindol-1,3-dione was dissolved in 0.5 mL of THF. 0.5 mL of methylamine aqueous solution was added. After the mixture was stirred overnight for 20 h, 50 mL of water and 50 mL of ethyl acetate were added to the reaction, which was then violently vibrated and isolated. The ethyl acetate layer was successively washed with 100 mL of saturated sodium bicarbonate aqueous solution and 100 mL of saturated sodium chloride aqueous solution, dried over 3 g of MgSO$_4$ for 1 h, and concentrated via a rotary evaporator to obtain a pale yellow oil.

Compound 9b (8-(2-(trifluoromethoxy)phenoxy)octyl-1-amine) was prepared with a process similar to that for preparing compound 9a.

Preparation of Compounds of the Present Invention

Example 1

N-cyano-N'-(6-(2-difluoromethoxy-5-chlorophenoxy)hexyl)-N"-(4-pyridyl) guanidine

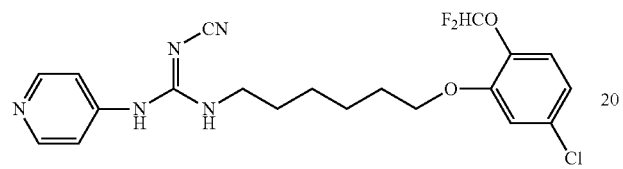

0.17 mL (1.2 mmol) of triethylamine and 140 mg (0.59 mmol) of 1-cyano-2-phenyl-3-(pyrid-4-yl)-isourea were added to a solution of 144 mg (0.49 mmol) of 6-(5-chloro-2-difluoromethoxy-phenoxy)hexyl-1-amine in 5.0 mL of ethanol (redistilled) under argon atmosphere with stirring, and the mixture was allowed to stir at room temperature for 2.0 h. The reaction was stopped, and the solvent was distilled off via a rotary evaporator. 25 mL of ethyl acetate and 20 mL of water were added to the residue. The organic layer was isolated, and the water layer was extracted with 20 mL×2 of ethyl acetate. The organic layers were combined, washed with 50 mL of saturated sodium bicarbonate aqueous solution, 50 mL of water and 50 mL of saturated saline, dried over anh. MgSO$_4$, filtered and concentrated. The residue was purified by preparative silica gel thin layer chromatography (mobile phase: chloroform: methanol=12:1) to obtain 115 mg of a pale yellow off-white needle-like solid. Yield 53.5%. MS([M-H]$^-$): 436.

The preparation method for compounds of examples 2-18 and comparative examples 1-4 are similar to that of example 1.

Example 2

N-cyano-N'-(6-(o-trifluoromethoxyphenoxy)hexyl)-N"-(3-pyridyl) guanidine

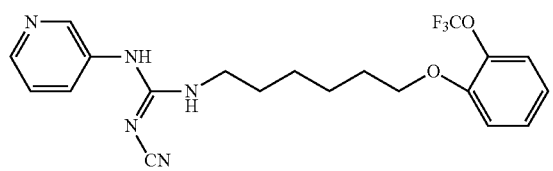

MS([M + H]$^+$): 422

Example 3

N-cyano-N'-(6-(m-trifluoromethoxyphenoxy)hexyl)-N"-(4-pyridyl) guanidine

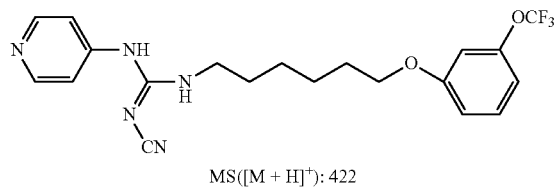 [SMILES: N#C/N=C(\NCCCCCCOc1cccc(OC(F)(F)F)c1)Nc1ccncc1]

MS([M + H]$^+$): 422

Example 4

N-cyano-N'-(6-(p-trifluoromethoxyphenoxy)hexyl)-N"-(4-pyridyl) guanidine

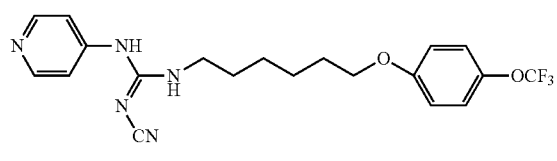

MS([M + H]$^+$): 422

Example 5

N-cyano-N'-(5-(o-trifluoromethoxyphenoxy)pentyl)-N"-(4-pyridyl) guanidine

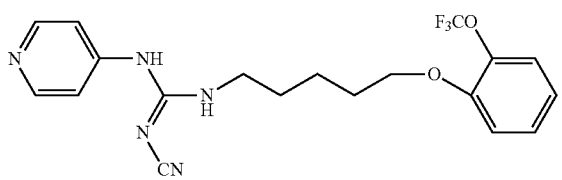

MS([M + H]$^+$): 408

Example 6

N-cyano-N'-(8-(o-trifluoromethoxyphenoxy)octyl)-N"-(4-pyridyl) guanidine

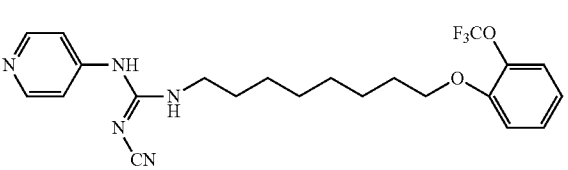

MS([M + H]$^+$): 450

Example 7

N-cyano-N'-(6-(2-trifluoromethoxy-4-bromophenoxy)hexyl)-N''-(4-pyridyl)guanidine

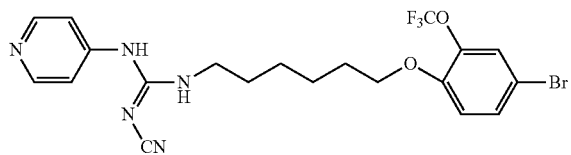

MS([M + H]$^+$): 501

$^1$H NMR (600M, DMSO-d$_6$) δ: 1.314-1.457 (m, 4H, CH$_2$), 1.516-1.563 (m, 2H, CH$_2$), 1.704-1.750 (m, 2H, CH$_2$), 3.265 (q, 2H, NH—CH$_2$, J$_1$=13.2, J$_2$=6.3), 4.062 (t, 2H, O—CH$_2$, J=12.6), 7.202-7.231 (m, 3H, phenyl, pyridyl), 7.547 (q, 1H, phenyl), 7.591-7.602 (m, 1H, phenyl), 7.835 (t, 1H, NH), 8.386 (d, 2H, pyridyl), 9.353 (bs, 1H, NH).

Example 8

N-cyano-N'-(6-(o-trifluoromethoxy phenylamino)hexyl)-N''-(4-pyridyl) guanidine

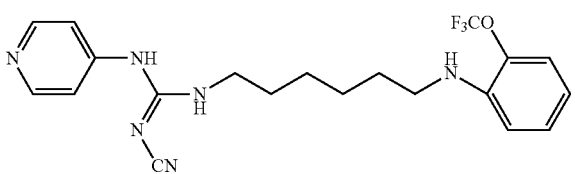

MS([M + H]$^+$): 421

Example 9

N-cyano-N'-(6-(o-trifluoromethoxybenzoyloxy)hexyl)-N''-(4-pyridyl) guanidine

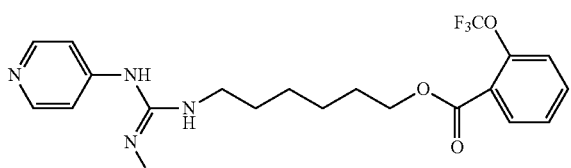

MS([M + H]$^+$): 450

Example 10

N-cyano-N'-(6-(2-difluoromethoxy-5-tert-butylphenoxy)hexyl)-N''-(4-pyridyl)guanidine

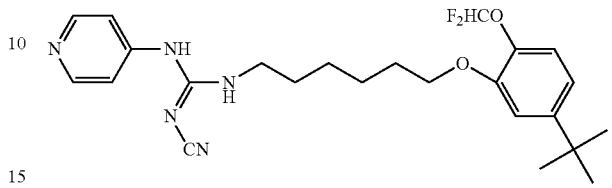

MS([M + H]$^+$): 460

Example 11

N-cyano-N'-(6-(o-trifluoromethoxyphenoxy)hexyl)-N''-(4-pyridyl) guanidine

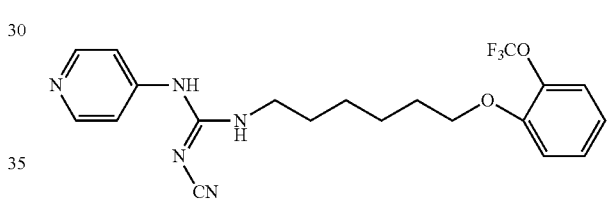

MS([M + H ]$^+$): 422

$^1$H NMR (600M, CDCl$_3$) δ: 1.431-1.489 (m, 2H, CH$_2$), 1.515-1.566 (m, 2H, CH$_2$), 1.630-1.676 (m, 2H, CH$_2$), 1.802-1.848 (m, 2H, CH$_2$), 3.379 (q, 2H, NH—CH$_2$), 4.009 (t, 2H, O—CH$_2$), 6.902-6.984 (m, 3H), 7.206-7.271 (m, 4H), 8.500 (d, 2H).

Example 12

N-cyano-N'-(6-(2-difluoromethoxy-4-chlorophenoxy)hexyl)-N''-(4-pyridyl)guanidine

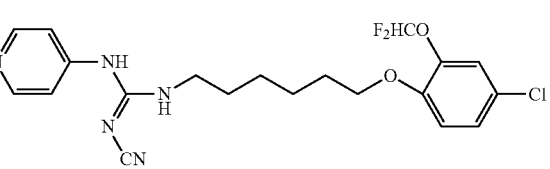

MS([M - H]$^-$): 436; MS([M + H]$^+$): 438

Example 13

N-cyano-N'-(6-(2-trifluoromethoxy-4-chlorophenoxy)hexyl)-N''-(4-pyridyl)guanidine

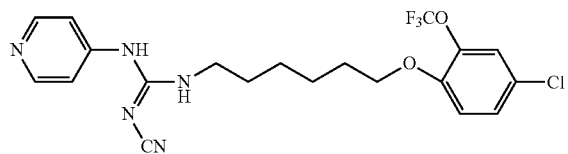

MS([M + H]$^+$): 456

Example 14

N-cyano-N'-(6-(2-trifluoromethoxy-4-nitrophenoxy)hexyl)-N''-(4-pyridyl)guanidine

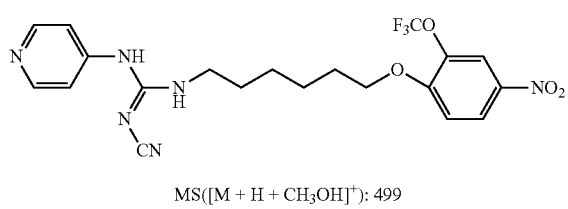 [SMILES: N#C/N=C(\NCCCCCCOc1ccc([N+](=O)[O-])cc1OC(F)(F)F)Nc1ccncc1]

MS([M + H + CH$_3$OH]$^+$): 499

Example 15

N-cyano-N'-(6-(2-trifluoromethoxy-4-fluorophenoxy)hexyl)-N''-(4-pyridyl)guanidine

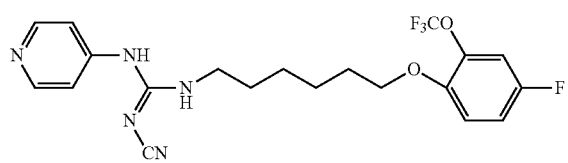

MS([M + H]$^+$): 440

Example 16

N-cyano-N'-(6-(5-methyl-2-difluoromethoxyphenoxy)hexyl)-N''-(4-pyridyl)guanidine

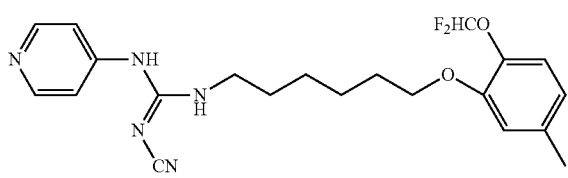

MS([M − H]$^-$): 416; MS([M + H]$^+$): 418

Example 17

N-cyano-N'-(6-(2-difluoromethoxyphenoxy)hexyl)-N''-(4-pyridyl) guanidine

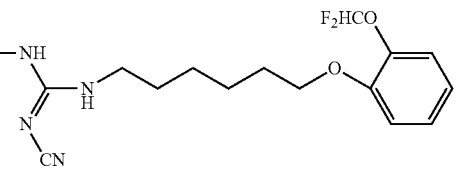

MS([M + H]$^+$): 404

Example 18

N-cyano-N'-(6-(2-difluoromethoxy-5-fluorophenoxy)hexyl)-N''-(4-pyridyl)guanidine

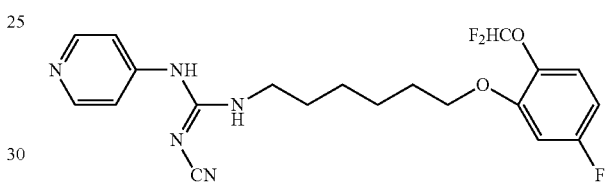

MS([M + H]$^+$): 422

Comparative Compound 1

N-cyano-N'-(5-(o-methoxyphenoxy)pentyl)-N''-(4-pyridyl) guanidine

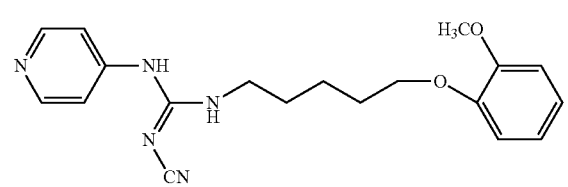

MS([M − H]$^-$): 352; MS([M + H]$^+$): 354

Comparative Compound 2

N-cyano-N'-(6-(4-chlorophenoxy)hexyl)-N''-(4-pyridyl) guanidine

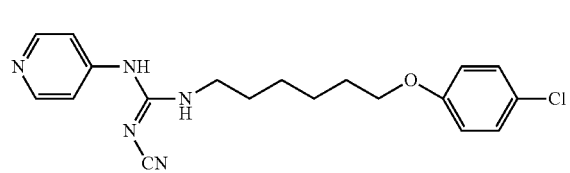 [SMILES: N#C/N=C(\NCCCCCCOc1ccc(Cl)cc1)Nc1ccncc1]

Comparative Compound 3

N-cyano-N'-(6-(2-chlorophenoxy)hexyl)-N"-(4-pyridyl) guanidine

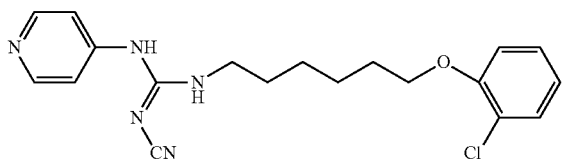 [SMILES: N#C/N=C(\NCCCCCCOc1ccccc1Cl)Nc1ccncc1]

Comparative Compound 4

N-cyano-N'-(6-(2-methoxyphenoxy)hexyl)-N"-(4-pyridyl) guanidine

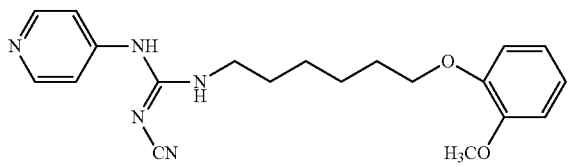

MS([M − H]$^-$): 366; MS([M + H]$^+$): 368

Pharmacological Activity Assay

This test was carried out using conventional operations in the art. Specifically, the following materials and methods were employed:

1. Test Compounds

Examples 1, 2, 4-7, 10-12 and 16, Comparative Compounds 1-4.

2. Cell Strains:

Human pancreatic cancer AsPC-1; human acute lymphocytic leukemia taxol-resistant cell strain CCRF-CEM/T; human adenocarcinoma of lung NCI-H1975; human pharyngeal squamous cell carcinoma Fadu; human B lymphoma BA25; human B lymphoma BA91; human B lymphoma BA127; human stomach cancer NCI-N87; human non-small cell lung cancer A549; human liver cancer SK-Hep-1; human lung cancer NCI-H460; human prostate cancer PC-3.

3. Methods:

3.1 Adherent Cells

The following cells were cultured under the following conditions, respectively:

AsPC-1: 90% RPMI1640, 10% FBS;
NCI-H1975: 90% RPMI1640, 10% FBS;
Fadu: 90% EMEM, 10% FBS;
NCI-N87: 90% RPMI1640, 10% FBS;
37° C., 5% $CO_2$, saturated humidity.

The cells were cultured until confluence, digested with a pancreatic enzyme, and prepared into a single cell suspension in a complete medium.

The cells were seeded in a 96-well microplate at a suitable concentration (AsPC-1: 8000 cells/well; NCI-H1975: 5000 cells/well; Fadu: 6000 cells/well; NCI-N87: 15000 cells/well), cultured overnight to render them adherent to the bottom.

A 2 mM stock solution was prepared by dissolving test compounds in DMSO, diluted with a base medium (without serum) to form a 20 μM or 2 μM 10× working solution which was diluted using a gradient of 1/3. During dilution, the concentration of DMSO was kept consistent. There were 8 dose groups in total. 20 μl of 10× compound working solution was added to the experimental well until the final volume of each well was 200 μl and the concentration of DMSO was 1‰. Meanwhile, a solvent control group (PC) without compounds (PC) and a solvent control group without cells and compounds (NC) were prepared. The cells were further cultured for 72 h.

Subsequently, the activity of cells was measured with a microculture tetrozolium (MTT method). Specifically, the medium in well was sucked out, a base medium containing 0.5 mg/ml MTT was added in an amount of 100 μl/well, and then the cell was further cultured for 3 h. The medium containing MTT was once again sucked out, 100 μl/well of DMSO was added to dissolve MTT crystal, and OD value at 490 nm was measured with an ELISA analyzer.

Inhibition rate of a compound was calculated as follows:

Inhibition rate=[1−(OD value of administration group−OD value of NC)/(OD value of PC−OD value of NC)]×100%

Inhibition rates were then plotted versus the logarithm of compound concentrations, and fitted with Logistic 4 parameter equation. The compound concentration corresponding to 50% inhibition rate in the curve was $IC_{50}$ value.

3.2 Suspension Cells

The cells were cultured under the following conditions:
complete medium: 90% RPMI1640, 10% FBS; 37° C., 5% $CO_2$, saturated humidity.

After cultured to the end of the logarithmic growth phase, the cells were diluted with the complete medium to the required concentration.

The cells were seeded in a 96-well microplate at a suitable concentration (CCRF-CEM/T: 20000 cells/well; BA25: 20000 cells/well; BA91: 60000 cells/well; BA127: 60000 cells/well).

A 2 mM stock solution was prepared by dissolving test compounds in DMSO, diluted with a base medium (without serum) to form a 20 μM or 2 μM 10× working solution which was diluted using a gradient of 1/3. During dilution, the concentration of DMSO was kept consistent. There were 8 dose groups in total. 12 μl of 10× compound working solution was added to the experimental well until the final volume of each well was 120 μl and the concentration of DMSO was 1‰. Meanwhile, a solvent control group without compounds (PC) and a solvent control group without cells and compounds (NC) were prepared. The cells were further cultured for 72 h.

Subsequently, the activity of cells was measured with a microculture tetrozolium (MTT method). Specifically, 30 μl/well of PBS containing 2.5 mg/ml MTT was added, and then the cells were cultured for another 3 h. 100 μl/well of triple lysis buffer (10% SDS, 5% isobutanol, 0.012 M HCl) was added, and the mixture was kept at room temperature to dissolve MTT crystal. OD value at 570 nm was measured with an ELISA analyzer.

Inhibition rate of a compound was calculated as follows:
Inhibition rate=[1−(OD value of administration group−OD value of NC)/(OD value of PC−OD value of NC)]×100%

Inhibition rates were then plotted versus the logarithm of compound concentrations, and fitted with Logistic 4 parameter equation. The compound concentration corresponding to 50% inhibition rate in the curve was $IC_{50}$ value.

4. Results 4.1 The growth inhibition effects of some compounds on Aspc-1 in vitro are shown in the following table 1.

TABLE 1

The growth inhibition effects of some compounds on Aspc-1 in vitro

| No. | IC$_{50}$ (nM) | No. | IC$_{50}$ (nM) |
|---|---|---|---|
| Control 2 | 19 | Control 3 | 7.2 |
| Control 4 | 7.3 | Control 1 | 135 |
| Example 11 | 2.1 | Example 12 | 2.3 |
| Example 16 | 0.9 | | |

It can be seen from table 1 that the growth inhibition effects of examples 11, 12 and 16 on human pancreatic cancer AsPC-1 in vitro are significantly superior to controls 1-4, which indicates a significant therapeutic effect of these compounds on pancreatic cancer.

4.2 The growth inhibition effects of some compounds on CCRF-CEM-T in vitro are shown in the following table 2.

TABLE 2

The growth inhibition effects of some compounds on CCRF-CEM-T in vitro

| No. | IC$_{50}$ (nM) | No. | IC$_{50}$ (nM) |
|---|---|---|---|
| Control 2 | 22 | Control 3 | 6.3 |
| Control 4 | 6.9 | Control 1 | 113 |
| Example 1 | 2.2 | Example 7 | 5.1 |
| Example 11 | 1.6 | Example 12 | 2.3 |
| Example 16 | 2.2 | | |

It can be seen from table 2 that the growth inhibition effects of examples 1, 7, 11, 12 and 16 on human acute lymphocytic leukemia taxol-resistant cell strain CCRF-CEM/T in vitro are significantly superior to controls 1-4, which indicates a significant effect of these compounds on human acute lymphocytic leukemia.

4.3 The growth inhibition effects of some compounds on BA25 in vitro are shown in the following table 3.

TABLE 3

The growth inhibition effects of some compounds on BA25 in vitro

| No. | IC$_{50}$ (nM) | No. | IC$_{50}$ (nM) |
|---|---|---|---|
| Example 2 | 4.4 | Example 4 | 12 |
| Example 5 | 7.3 | Example 6 | 5.6 |
| Example 7 | 6.3 | Example 11 | 1 |

It can be seen from table 3 that the IC$_{50}$ values of examples 2, 5-7 and 11 are significantly lower than that of example 4, which indicates that the compound with F-substituted methoxy at 2-position has a superior inhibition effect on human B lymphoma BA25 than the compound with F-substituted methoxy at para-position.

4.4 The growth inhibition effects of some compounds on FaDu in vitro are shown in the following table 4.

TABLE 4

The growth inhibition effects of some compounds on FaDu in vitro

| No. | IC$_{50}$ (nM) | No. | IC$_{50}$ (nM) |
|---|---|---|---|
| Control 2 | 11.7 | Example 1 | 1.2 |
| Example 7 | 4.7 | Example 10 | 2.4 |
| Example 11 | 1.5 | Example 12 | 2.8 |
| Example 16 | 1.3 | | |

It can be seen from table 4 that the inhibition effects of examples 1, 7, 10-12 and 16 on human pharyngeal squamous cell carcinoma Fadu are significantly superior to control 2.

4.5 The growth inhibition effects of some compounds on BA127 in vitro are shown in the following table 5.

TABLE 5

The growth inhibition effects of some compounds on BA127 in vitro

| No. | IC$_{50}$ (nM) | No. | IC$_{50}$ (nM) |
|---|---|---|---|
| Example 1 | 1.4 | Example 2 | 4.3 |
| Example 5 | 6.1 | Example 6 | 9.3 |
| Example 7 | 6.9 | Example 10 | 13 |
| Example 11 | 1.5 | Example 16 | 1.3 |
| Example 12 | 3.2 | | |

4.6 The growth inhibition effects of some compounds on BA91 in vitro are shown in the following table 6.

TABLE 6

The growth inhibition effects of some compounds on BA91 in vitro

| No. | IC$_{50}$ (nM) | No. | IC$_{50}$ (nM) |
|---|---|---|---|
| Example 1 | 2 | Example 2 | 2.7 |
| Example 5 | 6.9 | Example 6 | 9.6 |
| Example 7 | 5.8 | Example 10 | 3.5 |
| Example 11 | 1.5 | Example 16 | <1 |
| Example 12 | <1 | | |

4.7 The growth inhibition effects IC$_{50}$ (nM) of some compounds on tumour cells in vitro are shown in the following table 7.

TABLE 7

The growth inhibition effects IC$_{50}$ (nM) of some compounds on tumour cells in vitro

| No. | NCI-H1975 | NCI-N87 | A549 | SK-Hep-1 | NCI-H460 | PC-3 |
|---|---|---|---|---|---|---|
| Control 2 | 54 | 14 | 22 | 16 | 83 | 2.5 |
| Control 4 | 15.5 | 6.6 | 9.9 | | 38 | 2.4 |
| Example 11 | 5.3 | 1.5 | 3 | 2.3 | 8 | 0.2 |

The above table indicates that the growth inhibition effects of example 11 on six tumour cell models in vitro are much better than those of controls 2 and 4.

It should be understood that each specific technical feature and element (such as compound, structure unit of compound, group, composition, combination) as described for some particular aspects, embodiments and examples are not limited to these particular aspects, embodiments and examples. In other words, a person skilled in the art should understand that each specific technical feature and element can be used in other aspects, embodiments and examples in the present application, unless they conflict with each specific technical feature and element (such as compound, structure unit of compound, group, composition, combination) of other aspects, embodiments and examples in the present application.

Meanwhile, unless conflicting with each other, all the technical features and elements (including all the steps in the methods) as disclosed in the present application can be combined in any way to form different technical solutions of the invention.

What is claimed is:

1. A compound of formula (I) or a pharmaceutically acceptable salt thereof,

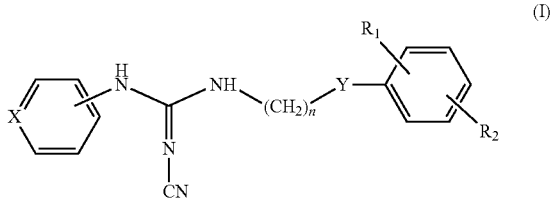

wherein: X is N or CH;
n is an integer from 3 to 10;
Y is —O—, —S—, —NR$_3$—, —OC(O)— or —NR$_3$C(O)—, wherein R$_3$ is H or C$_{1-6}$ alkyl;
R$_1$ is methoxy substituted with one or more F or Cl;
R$_2$ is H, C$_{1-6}$ alkyl, C$_{1-6}$ alkoxy, hydroxy, cyano, nitro, formamido, aminosulfonyl, halogen, C$_{1-6}$ alkyl optionally substituted with halogen, or C$_{1-6}$ alkoxy optionally substituted with halogen.

2. The compound or pharmaceutically acceptable salt thereof of claim 1, wherein
X is N;
n is an integer from 4 to 8;
Y is —O—, —S—, —NR$_3$—, —OC(O)— or —NR$_3$C(O)—, wherein R$_3$ is H or C$_{1-6}$ alkyl;
R$_1$ is methoxy substituted with at least two F;
R$_2$ is H, C$_{1-6}$ alkyl, nitro, halogen, or C$_{1-6}$ alkyl optionally substituted with halogen.

3. The compound or pharmaceutically acceptable salt thereof of claim 1, wherein
X is N;
n is an integer from 4 to 8;
Y is —O—, —NH— or —OC(O)—;
R$_1$ is methoxy substituted with at least two F at 2-position of the benzene ring;
R$_2$ is H, C$_{1-4}$ alkyl, nitro, or halogen.

4. The compound or pharmaceutically acceptable salt thereof of claim 1, wherein
X is N;
n is an integer from 4 to 8;
Y is —O—, —NH— or —OC(O)—;
R$_1$ is OCF$_3$ or OCHF$_2$ at 2-position of the benzene ring;
R$_2$ is H, C$_{1-4}$ alkyl, F, Cl, or Br.

5. The compound or pharmaceutically acceptable salt thereof of claim 1, wherein
X is N;
n is an integer from 4 to 8;
Y is —O—;
R$_1$ is OCF$_3$ or OCHF$_2$ at 2-position of the benzene ring;
R$_2$ is H, C$_{1-4}$ alkyl, F, Cl, or Br.

6. The compound or pharmaceutically acceptable salt thereof of claim 1, which is selected from the group consisting of:
N-cyano-N'-(6-(2-difluoromethoxy-5-chlorophenoxy)hexyl)-N''-(4-pyridyl)guanidine;
N-cyano-N'-(6-(o-trifluoromethoxyphenoxy)hexyl)-N''-(3-pyridyl)guanidine;
N-cyano-N'-(6-(m-trifluoromethoxyphenoxy)hexyl)-N''-(4-pyridyl)guanidine;
N-cyano-N'-(6-(p-trifluoromethoxyphenoxy)hexyl)-N''-(4-pyridyl)guanidine;
N-cyano-N'-(5-(o-trifluoromethoxyphenoxy)pentyl)-N''-(4-pyridyl)guanidine;
N-cyano-N'-(8-(o-trifluoromethoxyphenoxy)octyl)-N''-(4-pyridyl)guanidine;
N-cyano-N'-(6-(2-trifluoromethoxy-4-bromophenoxy)hexyl)-N''-(4-pyridyl)guanidine;
N-cyano-N'-(6-(o-trifluoromethoxyphenylamino)hexyl)-N''-(4-pyridyl)guanidine;
N-cyano-N'-(6-(o-trifluoromethoxybenzoyloxy)hexyl)-N''-(4-pyridyl)guanidine;
N-cyano-N'-(6-(2-difluoromethoxy-5-t-butylphenoxy)hexyl)-N''-(4-pyridyl)guanidine;
N-cyano-N'-(6-(o-trifluoromethoxyphenoxy)hexyl)-N''-(4-pyridyl)guanidine;
N-cyano-N'-(6-(2-difluoromethoxy-4-chlorophenoxy)hexyl)-N''-(4-pyridyl)guanidine;
N-cyano-N'-(6-(2-trifluoromethoxy-4-chlorophenoxy)hexyl)-N''-(4-pyridyeguanidine;
N-cyano-N'-(6-(2-trifluoromethoxy-4-nitrophenoxy)hexyl)-N''-(4-pyridyl)guanidine;
N-cyano-N'-(6-(2-trifluoromethoxy-4-fluorophenoxy)hexyl)-N''-(4-pyridyl)guanidine;
N-cyano-N'-(6-(5-methyl-2-difluoromethoxyphenoxy)hexyl)-N''-(4-pyridyl)guanidine;
N-cyano-N'-(6-(2-difluoromethoxyphenoxy)hexyl)-N''-(4-pyridyl)guanidine; and
N-cyano-N'-(6-(2-difluoromethoxy-5-fluorophenoxy)hexyl)-N''-(4-pyridyl)guanidine.

7. The compound of claim 1, wherein R$_1$ is methoxy substituted with at least two F or Cl at 2- or 3-position of the benzene ring.

8. The compound of claim 2, wherein R$_1$ is methoxy substituted with at least two F at 2-position of the benzene ring.

9. A pharmaceutical composition comprising a therapeutically effective amount of the compound or pharmaceutically acceptable salt thereof of claim 1 and a pharmaceutically acceptable carrier.

10. The pharmaceutical composition of claim 9, wherein the pharmaceutical composition is used for treating cancer.

11. A method for preparing the compound of claim 1, comprising reacting a compound of formula (II)

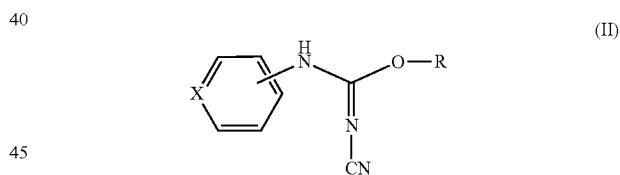

with a compound of formula (III)

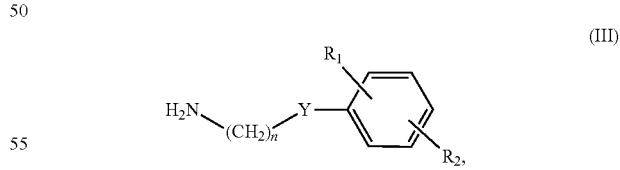

wherein, R is C$_{1-6}$ alkyl or aryl or aryl substituted with halogen or C$_{1-6}$ alkyl, X, Y, n, R$_1$ and R$_2$ have the same meanings as defined above, and
optionally, converting the resulting compound of formula (I) into a pharmaceutically acceptable salt thereof.

12. The method of claim 11, wherein the reaction of the compound of formula (II) with the compound of formula (III) is carried out in the presence of a base.

13. A method for inhibiting growth of a tumour cell, comprising administering to the tumour cell an inhibitory effective amount of the compound of claim 1 wherein the tumour is selected from the group consisting of pancreatic cancer, acute lymphocylic leukemia, lung cancer, -pharyngeal squamous cell carcinoma, lymphoma, stomach cancer, breast cancer, melanoma, neuroendocrine tumour, intestinal cancer, multiple myeloma, fibrosarcoma, prostate cancer and liver cancer.

14. A method for treating a tumour in a subject, comprising administering to the subject in need thereof a therapeutically effective amount of the compound of claim 1 wherein the tumour is selected from the group consisting of pancreatic cancer, acute lymphocylic leukemia, lung cancer, pharyngeal squamous cell carcinoma, lymphoma, stomach cancer, breast cancer, melanoma, neuroendocrine tumour, intestinal cancer, multiple myeloma, fibrosarcoma, prostate cancer and liver cancer.

15. The method of claim 13, wherein the tumour is adenocarcinoma of lung.

16. The method of claim 14, wherein the tumour is adenocarcinoma of lung.

\* \* \* \* \*